United States Patent [19]

Lapidot et al.

[11] Patent Number: 5,438,405
[45] Date of Patent: Aug. 1, 1995

[54] DEVICE AND METHOD FOR TESTING OPTICAL ELEMENTS

[75] Inventors: Moshe Lapidot, Kiryat Bialik; Samuel Liran, Haifa; Amit Stekel, Rehovot, all of Israel

[73] Assignee: Optomic Technologies Corporation, LTD, Migdal Haemek, Israel

[21] Appl. No.: 15,006

[22] Filed: Feb. 9, 1993

[30] Foreign Application Priority Data

Feb. 17, 1992 [IL] Israel ......................... 100972

[51] Int. Cl.6 ............................................. G01N 21/15
[52] U.S. Cl. ............................. 356/239; 356/431; 356/124
[58] Field of Search ............. 356/239, 124, 240, 237, 356/429-431

[56] References Cited

U.S. PATENT DOCUMENTS

| | | | |
|---|---|---|---|
| 3,788,749 | 1/1974 | George | 356/239 |
| 3,813,173 | 5/1974 | Teter | 356/239 |
| 3,892,494 | 7/1975 | Baker et al. | 356/239 |
| 3,988,068 | 10/1976 | Spragu | 356/124 |
| 4,815,844 | 3/1989 | Schmalfuss et al. | 356/124 |
| 4,822,165 | 4/1989 | Schmalfuss et al. | 356/239 |
| 4,841,139 | 6/1989 | Schmalfus et al. | 250/223 R |

*Primary Examiner*—William Mintel
*Assistant Examiner*—Alexander Oscar Williams
*Attorney, Agent, or Firm*—Keck, Mahin & Cate

[57] ABSTRACT

A system for grading and evaluating optical elements, such as lenses, filters, reticules and the like, where the tested element is scanned by at least one wedge shaped light beam, which has an angle of about 5 degrees to 35 degrees, and which intersects the surface of the optical element in the form of a narrow rectangle, and at an angle with the surface of the element. Beyond the optical element there is arranged a rotating mask which rotates synchronized with the rotating light beam, so that no direct light reaches an array of photoelements positioned beyond the mask, which array receives light pulses resulting from surface defects and internal defects of the tested optical element. The light signals reaching the said array are evaluated and thus the quality of the optical element is deduced.

13 Claims, 4 Drawing Sheets

DEVICE AND METHOD FOR TESTING OPTICAL ELEMENTS

FIELD OF INVENTION

The invention relates to a system for testing optical elements, made of optical material so as to determine the presents of any defects, and to decide whether such elements are of adequate quality or have to be discarded.

The system is suited to test lenses, over a wide range of diopters, possibly also with cylindrical components. This includes various types of lenses, such as progressive lenses, aspheric ones, optical filters, etc.

The system is suited for the testing of surface defects and also for detecting other internal faults. The system is suitable for use in the inspection of optical elements during the production process, and for the grading of such elements.

BACKGROUND OF THE INVENTION

Optical components must be tested prior to their utilization. Conventionally, the testing of optical components is carried out by trained personnel by visual manual inspection. This approach is not quantitative in nature, and thus can not be carried out objectively and reliably. The performance varies with different inspectors and with the same inspector from time to time.

Efforts have been made to develop methods and devices for automatic and objective testing of transparent optical components. The following patents deal with subject matter: DE Pat. No. 3620146 (U.S. Pat. No. 4,841,139); DE Pat. No. 3620108 (U.S. Pat. No. 4,822,165); DE Pat. No. 3620129 (U.S. Pat. No. 4,815,844); DD Pat. No. 241120; U.S. Pat. No. 3,988,068; UK Pat. No. 34851/72 (U.S. Pat. No. 3,892,494).

These have significant drawbacks. The proposed solutions in these patents are not cost effective in the sense that they are too complex and slow for use in mass production lines. Systems that utilize complex scanning means are too slow to inspect hundreds of lenses per hour, as required in such lines.

Another problem arises from sensitivity to various lens parameters. The lenses may be positive or negative, spherical, cylindrical or both, aspheric and progressive. Most solutions have difficulties in adapting to different batches of lenses that have different geometrical properties, using different illumination geometries for each batch, thus consuming time in arranging the set up between different batches.

Yet, a serious problem arises from the illumination methodology itself, patents using light sources with characteristics that are different in nature from the recommendation in the various cosmetic standards, lead to differences in the defects appearance in respect to their appearance in daily use of lenses, thus causing to a serious reliability problem by producing artifacts that are not detectable in daily use. Furthermore, some of the illumination methods are sensitive to different defects locations causing difficulties in simultaneously detecting defects in both faces and inside the lens and therefore resulting in non homogeneous yield.

The present patent overcomes these difficulties and shortcomings of the said previous patents.

SUMMARY OF THE INVENTION

There is provided a system for testing optical transparent elements, which may have cylindrical component, progressive lenses, aspheric lenses, etc., so as to detect surface and internal defects. There is further provided a method for such testing. The system can be used in a mass production and gives rapid and reliable results. Means are advantageously provided for the automatic evaluation of the test results and for the grading of the optical elements. The basic features of the method of the invention comprises a scanning of the lens by the means of one, or more light beams, so that any surface or internal defects scatter the light of the incident beam or beams, which scattered light is collected by a photo sensitive element, such as a CCD camera, the output of which is indicative of the presence or the absence of the defects, and the gravity of such defects.

The method is applicable for the testing of lenses having a wide range of diopters, and which may have a variety of cylindrical components, and for the automatic reliable and rapid evaluation so as to determine any possible production defects. According to the method of the invention the surface of the lens is scanned sector wise so as to cover the entire surface. Preferably the system provides one or more wedge shaped light beams, which are rotated and which illuminate simultaneously the same narrow strip of the lens surface. Any defect of the lens, such as surface scratches, irregularities and the like, scatter some of the light toward a light sensitive element, which is generally a suitable CCD camera, while in the absence of such defects light coming from the light source will not reach such a photoelectric array.

The wedge shaped light beam aimed at the diameter of the lens is incident onto this diameter at a rather wide range of incidence angles, so that the light is scattered by a variety of flaws, which light passes through a suitable mask, which rotates synchronously with the scanning light beam and only light due to scattering from flaws, passes said mask and reaches the said CCD camera. The mask allows illuminating the tested lens at relatively small angles without imaging the light source, and also blocks out images resulting from internal light reflections between the lens surfaces. The method gives reliable results and can be used to test defects according to the ANSI, DIN and other standards.

The CCD camera is operated in a single shot mode integration time can be controlled. The time is advantageously set to a period that equals one or more whole scanning revolutions, and at the end of such scan or sequence of scans, the information collected in the camera frame is fed as standard video to a frame grabber and evaluation system.

Advantageously there is employed an image processing algorithm, which enhances the lens flaws, recognizes them, evaluates them according to predetermined parameters and decides whether to accept or to discard the tested lens.

According to a preferred embodiment, the testing sequence can be actuated by the insertion of the lens to be tested in place in the test system.

The use of a mono shot camera simplifies the computation and improves the signal to noise ratio. It is advantageous to hold the lens in place, while the light beam is rotated so as to scan the lens surface by wedge shaped beam or beams. The lenses are advantageously tested by means of visible light, i.e. over a wide range of wavelengths, which is closest to the conditions under which the lens is used in spectacles or the like.

BRIEF DESCRIPTION OF THE DRAWINGS

The system and method of the invention are described by way of illustration, in a non restrictive manner, with reference to the inclosed drawings, which are schematic and not according to scale, in which.

DETAILED DESCRIPTION OF THE PREFERRED EMBODIMENT

Although the testing of the optical elements can be carried out by means of a single rotating mirror, the invention is illustrated by means of a system where two such parallel wedge shaped light beams are directed at the diameter of the lens. An important part of the system is the rotation mechanism, which comprises the two sub systems LS, the light source, and rotating light transformer and scanning device, LTS. The system further comprises the imaging system IS.

Figure 1:
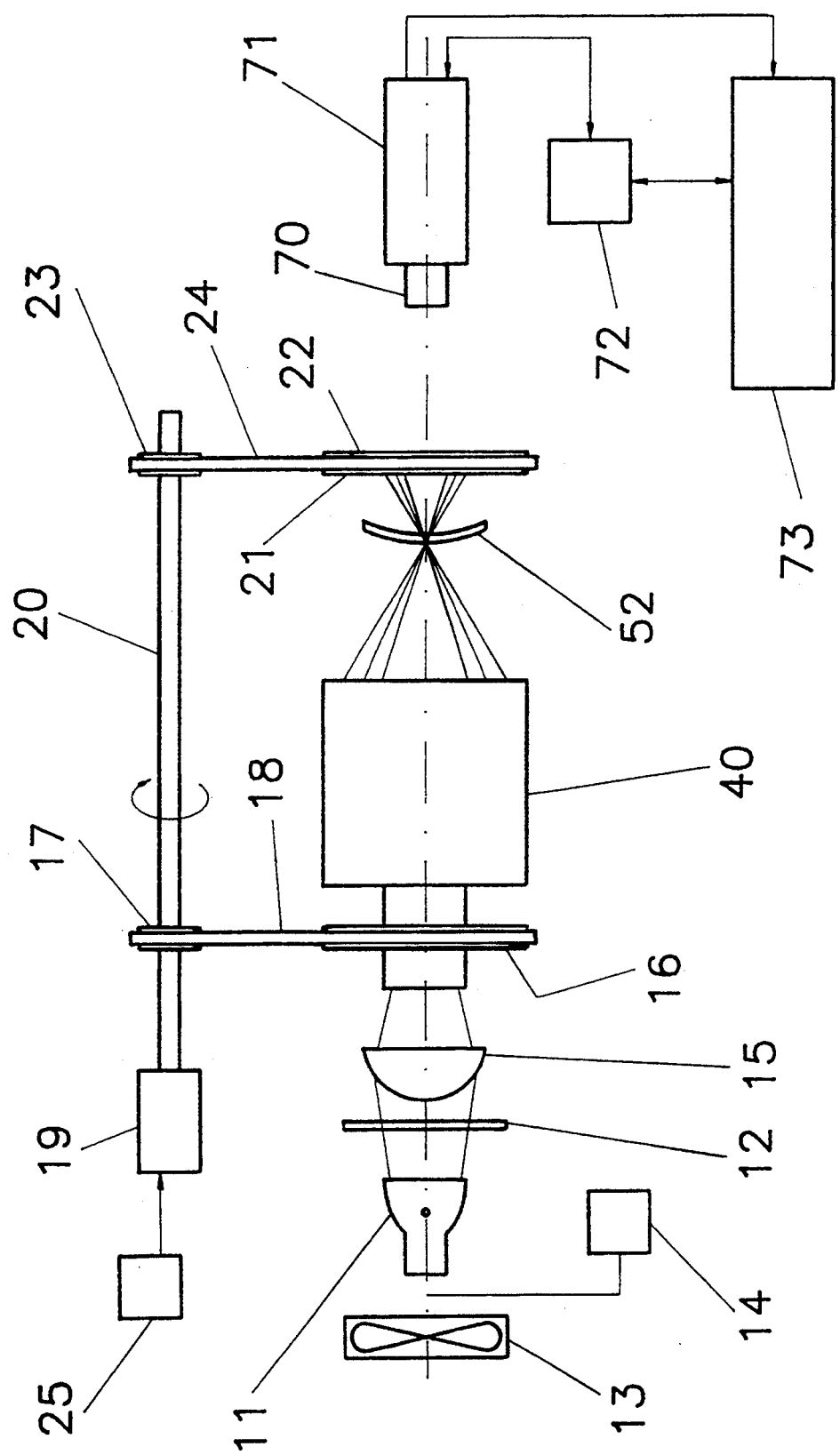
FIG. 1 is a schematic side view of a system of the invention.

As shown in FIG. 1, the system of the invention comprises a lamp 11, a heat absorbing filter 12, a fan 13 for removing heat, an adjustable power supply 14. The light combing out of the lamp passes through the condenser 15 and enters the LTS 40, which is driven by the means of the timing wheel 16, which is connected with the timing wheel 17 by timing belt 18, this mechanism being actuated by motor 19 driven by motor controller 25. The motor is connected to shaft 20, the end of which is connected with similar mechanism, comprising a rotating mask 21, which is actuated via timing wheels 22 and 23, connected by belt 24. The light coming from the condenser 15 passes through rotating light transformer and scanning unit 40.

Figure 2:
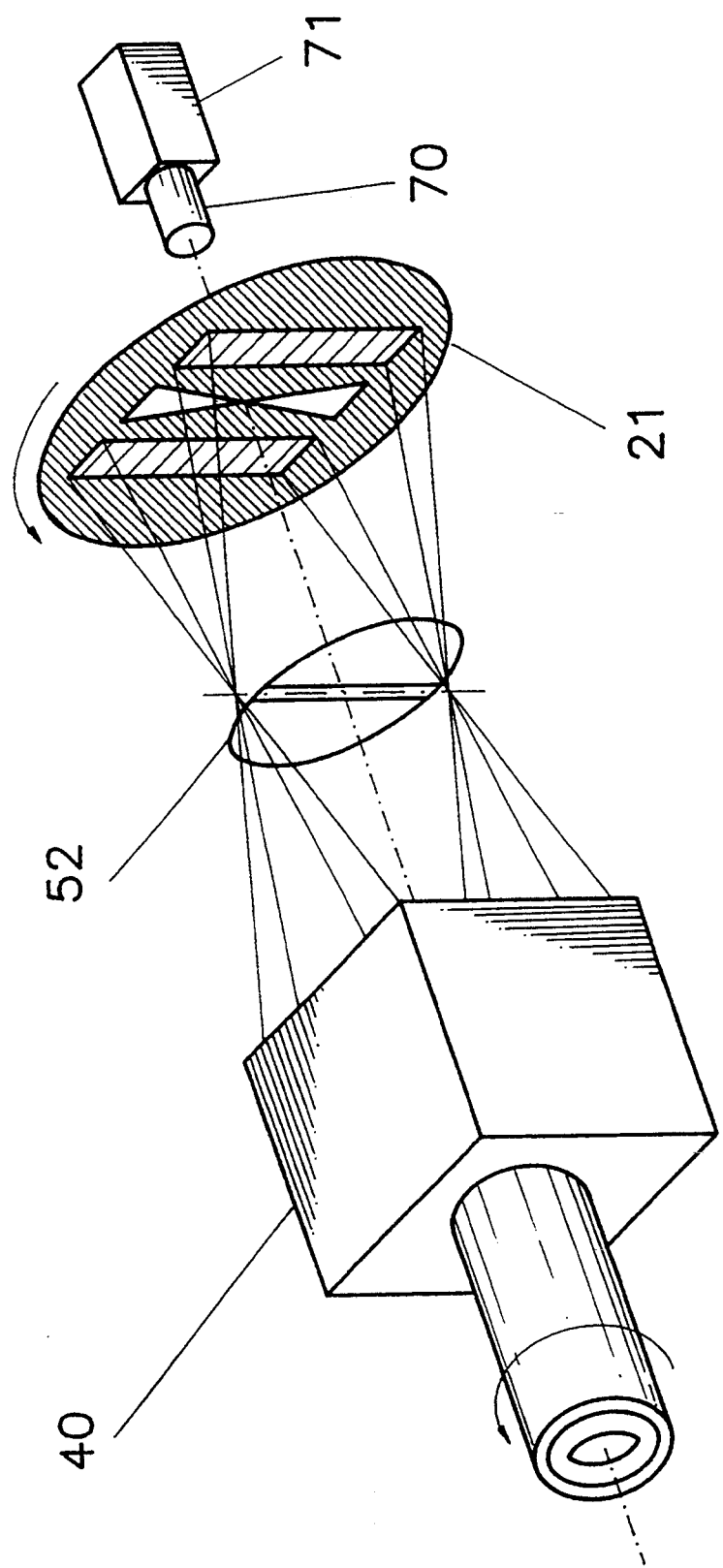
FIG. 2 is a perspective view of the rotating light transformer and scanning device of the system.

FIG. 2 is a perspective view, showing the arrangement of part of the system set out in FIG. 1, where the parts are designed by identical numbers.

Figure 3:
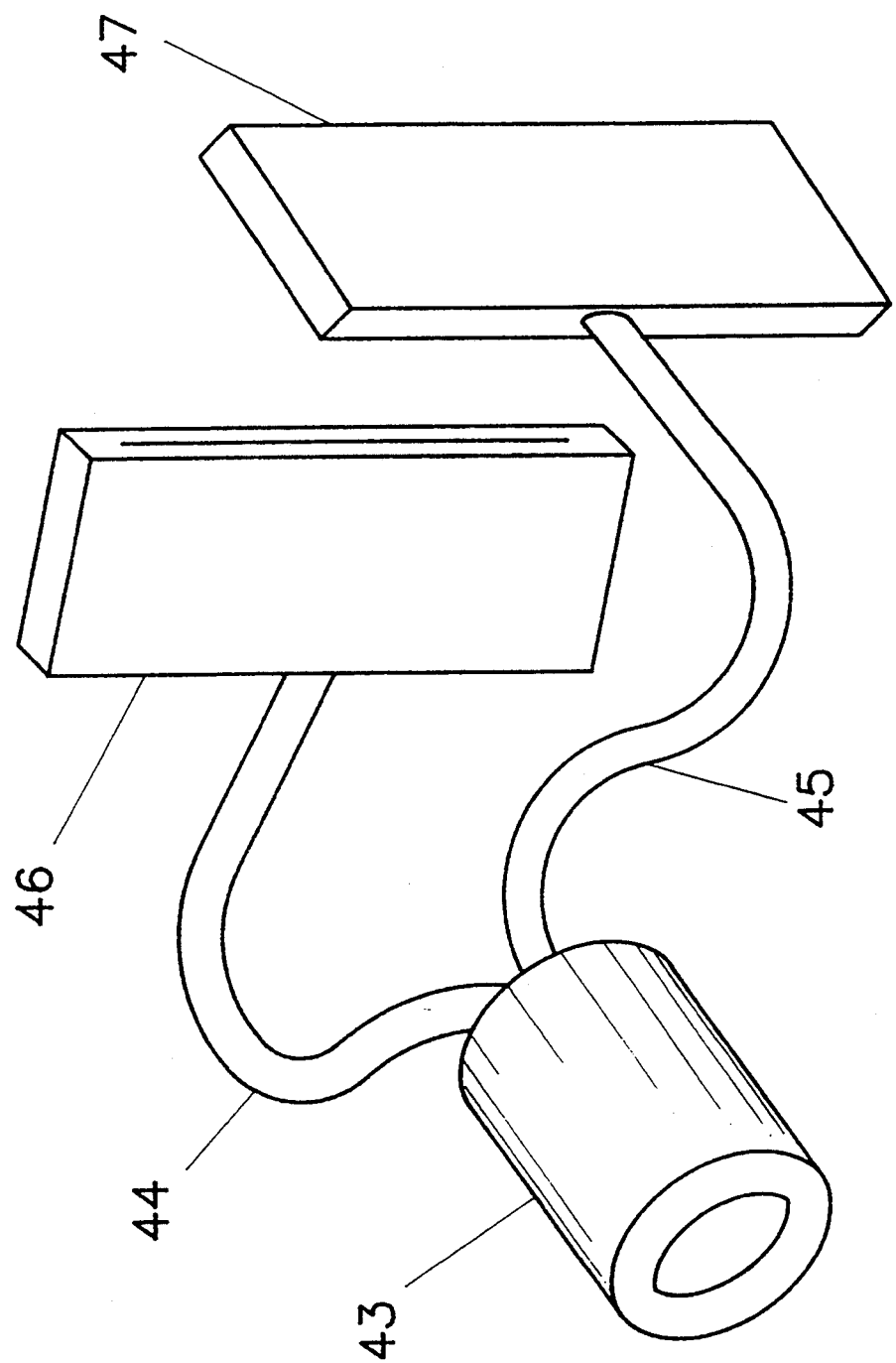
FIG. 3 is a perspective view of the sub system for producing two linear light beams parallel with each other in a plane.
Figure 4:
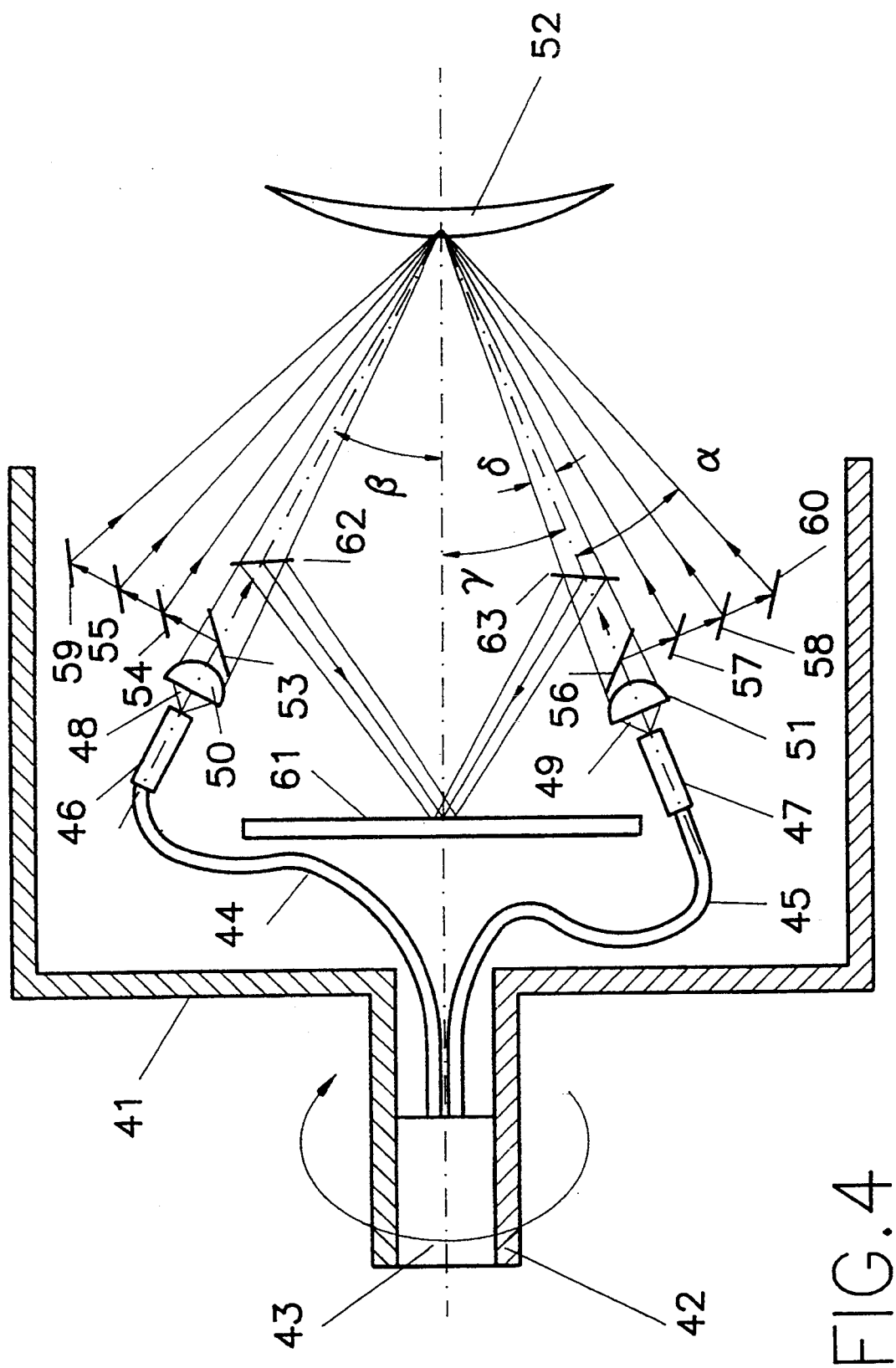
FIG. 4 is a sectional side view of the preferred rotating light source and beams incident on the lens being tested.

One embodiment of which is shown in FIG. 3 and 4 where 41 is a housing, the entry port of which, 42 is a hollow shaft housing the round light entrance member 43 of the light transformer, which passes the light via fiber bundles 44 and 45 to members 46 and 47, which emits the light linearly towards cylindrical lenses 50 and 51, which focus the light beams 48 and 49, in the vicinity of the frontal surface of the tested lens 52, in various angles and intensities which are set by using to two sets of three at the imaging system IS, which comprises a lens 70, a video camera 71, camera timing control 72, and image grabber and processor 73. The only light that reaches the CCD in the camera is the scattered light from the imperfections of the tested optical element. Each of the light beams 48 and 49, after being condensed by the cylindrical lenses 50 and 51, are split into four narrow beams by means of three beam splitters and one front surface mirror, thus creating wide light beams comprised of four narrow beams of d degrees angles separated by 2d angles to form 8d=a degrees angles.

The wide beams are tilted toward the systems optical axis in b and g degrees where g=b+d.

The system advantageously comprises beam splitters 62 and 63, which reflect back part of the light beams towards the dark background 61. The degree of illumination of the background is easily controlled by varying at will the coefficients of transmittance of the beam splitters. The partial illumination of the dark background is a requirement of certain standard of lens testing methods.

When two light beam groups are used they illuminate the lens simultaneously, at the angles b and g, by adjusting these angles, the illumination can be made to vary within a rather wide range of angles. Generally the angle a will be in the range of about 20° to about 35°. Angles b and g will generally be in the range from 15° to about 25°. The importance of the angles of the incident beams is in that various types of defects are more sensitive to illumination at a given angle than at another, and thus by using various angles of the light beams, the detection capability of the system is enhanced.

A system was constructed according to the above principles, and the following data are to be constructed in a non restrictive manner. According to the nature of the tested optical element, such as type of lens, its diameter, etc, variations and modifications of the system may be restored to, and components with widely different values can be used.

As light source there was used a 50 W halogen projector, with its main light spectrum in the 400 to 800 nm range. The bundles of optical fibers have a diameter of about 8.5 mm, and an effective surface area of about 56 mm. Fibers having a uniform attenuation of light over the spectrum 400 to 1200 nm was used. A wide range of rotation speeds can be used, which will generally be in the range of from about 125 RPM to about 1500 RPM. Good results were obtained with a model where the rate of revolution was 375 RPM.

There is used a 15 mm focal length condenser, and the mask is as illustrated in FIG. 2. As the surface area of the inspected lens is curved, the linear light beam directed at the diameter of the lens spreads out from the center towards the edge of the lens. This spread forms on the lens surface two illumination sectors. These sectors and the mask sectors rotate synchronously. The opening angle of the mask sectors is dictated by the said light spread. The two lenses used for the focusing of the light beams inside the inspected lens are cylindrical lenses of focal lengths 12 mm. The opening angles of each of the two beam groups was 32°, and the angle b and g were 15° and 19° respectively. There was used a CCD camera of the PULNIX 765E type, with a lens f=25 mm, D=f25 mm at its front. The principle of the operation of the camera timing and exposure control is as follows:

The camera is provided with integration time control means. The integration period continues as long as the integration signal is present. Information gathered in the CCD passes through the image grabber in standard video format, starting with the first vertical pulse after cessation of the integration signal.

There was used an image grabbing and processing subsystem which consists of MATROX—Image series installed in an IBM/AT compatible computer, and evaluation of the incoming signals resulting from lens imperfections was carried out with the help of a suitable algorithm, using conventional techniques of image processing and evaluation.

The described method can be alternatively realized using any optical and/or electro optical combination to implement the said optical element illumination and evaluation method.

We claim:

1. A method for rapid and accurate evaluation of optical lenses being tested, so as to detect surface and other defects and grade the lenses according to predetermined criteria, comprising the steps of:
   generating a linear wedge-shaped light beam of white light,
   illuminating a lens being tested by focusing the beam onto a diameter of the lens to cause the lens to intersect with a rectangular beam,
   rotating the beam with respect to the lens being tested, scanning an entire surface of the lens being tested at least once while blocking out direct light so that the direct light does not reach a CCD located on an axis behind the lens,
   passing light resulting from lens defects via a mask rotated in a manner synchronized with rotation of the light beam,
   directing resulting signals at said CCD,
   passing the resulting signals to an image grabbing and evaluation unit, and
   evaluating lens quality.

2. A method according to claim 1, wherein light scattered by imperfections in the lens being tested is passed via the mask having openings in the form of segments rotated in synchronization with rotation of the light beam.

3. A method according to claim 1, wherein an opening angle of the linear wedge-shaped beam of white light focused onto the diameter of the lens being tested is from about 5 degrees to about 35 degrees and an angle between the center of the beam with respect to the axis of the lens is from about 10 degrees to about 25 degrees.

4. A method according to claim 1, wherein said light beam is one of at least two wedge-shaped beams of white light which are aimed simultaneously at the diameter of the lens being tested.

5. A method according to claim 4, wherein angles of the at least two beams with respect to an optical axis are different, each of the angles being between 5 degrees and 35 degrees.

6. A method according to claim 1, wherein the light beam is rotated about a center of the lens being tested to scan its entire surface.

7. A system for lens grading and evaluation according to severity of surface and internal defects comprising:
   a light source,
   holding means for holding an optical lens being tested with its optical axis aligned with an optical axis of the system,
   means for directing a wedge-shaped light beam so as to intersect a diameter of the lens being tested at the diameter in the form of a narrow rectangular beam which intersects a surface of the lens being tested at an angle therewith,
   means for rotating said wedge-shaped light beam in synchronization with a mask located after the lens and an array of photosensitive elements arranged after said mask and facing the mask so that (1) rotation of the light beam sweeps the light beam over an entire surface of the lens being tested and (2) direct light is prevented from reaching the photosensitive elements so that the photosensitive elements receive only light signals due to scattering of light caused by defects of the optical lens being tested, and
   means for evaluating the light signals.

8. A system according to claim 7, wherein the wedge-shaped light beam has an opening angle of from about 5 to 35 degrees.

9. A system according to claim 7, wherein an angle of the light beam with respect to the optical axis varies between 10 and 25 degrees.

10. A system according to claim 7, wherein said light beam is one of two rotating wedge-shaped beams intersecting the diameter of the lens being tested used for illumination.

11. A system according to claim 10, wherein said light beam is one of two rotating wedge-shaped beams rotated so as to intersect the lens being tested at different angles of incidence.

12. A system according to claim 7, wherein an axis of a light beam from said light source is coaxial with a center of the lens being tested but routed and manipulated so that none of the direct light reaches the array of photosensitive elements as the light beam sweeps over the surface of the lens being tested.

13. A system according to claim 7, wherein light from the light source is conveyed via optical fibers and converted to at least one of said wedge-shaped beams of white light and the means for rotating said wedge-shaped light beam incident on the diameter of the optical lens being tested allows only passage of light scattered by imperfections in the optical lens being tested.

* * * * *